United States Patent [19]

Lukacsko et al.

[11] Patent Number: 5,260,333
[45] Date of Patent: Nov. 9, 1993

[54] EFFECT OF A COMBINATION OF A TERBUTALINE, DIPHENHYDRAMINE AND RANITIDINE COMPOSITION ON GASTROINTESTINAL INJURY PRODUCED BY NONSTEROIDAL ANTI-INFLAMMATORY COMPOSITIONS

[75] Inventors: Alison B. Lukacsko, Robbinsville; Joseph J. Piala, Metuchen, both of N.J.

[73] Assignee: Bristol Myers Squibb Company, New York, N.Y.

[21] Appl. No.: 865,730

[22] Filed: Apr. 9, 1992

Related U.S. Application Data

[63] Continuation of Ser. No. 598,580, Oct. 15, 1990, abandoned, which is a continuation of Ser. No. 243,225, Sep. 2, 1988, abandoned, which is a continuation of Ser. No. 894,982, Aug. 11, 1986, abandoned.

[51] Int. Cl.$^5$ .................... A61K 31/34; A61K 31/135
[52] U.S. Cl. .................... 514/471; 514/648; 514/649; 514/653; 514/654; 514/925; 514/926
[58] Field of Search .............. 514/557, 162, 165, 461, 514/925, 648, 927, 916, 161, 653, 649, 648, 654; 424/10, 471

[56] References Cited

U.S. PATENT DOCUMENTS

| | | | |
|---|---|---|---|
| 4,230,717 | 10/1980 | Locelace | 514/396 |
| 4,279,906 | 7/1981 | Frosch | 514/223 |
| 4,522,826 | 6/1985 | Sunshine et al. | 514/222 |
| 4,552,899 | 11/1985 | Sunshine et al. | 514/568 |
| 4,567,179 | 1/1986 | Lombardino | 514/225 |
| 4,579,846 | 4/1986 | Crawford et al. | 514/450 |
| 4,636,498 | 1/1987 | LaMattina | 514/222 |
| 4,672,061 | 6/1987 | Crawford et al. | 514/226.5 |
| 4,757,060 | 7/1988 | Lukacsko et al. | 514/162 |

FOREIGN PATENT DOCUMENTS 2120938 12/1983 United Kingdom ............... 514/161

OTHER PUBLICATIONS

Goodman and Gilman, The Pharmacological Basis of Therapeutics, 7th ed. (1985) pp. 149, 172–175.
*Facts and Comparisons,* p. 173a (Aug. 1977); p. 211 (May 1977); pp. 211b and 214b (Jul. 1976).
*The Merck Index,* 10th Ed. (1983), p. 1080, No. 7364.

*Primary Examiner*—Frederick E. Waddell
*Assistant Examiner*—T. J. Criares
*Attorney, Agent, or Firm*—Anthony M. Santini

[57] ABSTRACT

Pharmaceutical composition and process for administering NSAIDs with a combination of beta-adrenergic agonist and certain $H_1$-and $H_2$-receptor blockers which protect against injury to the gastrointestinal tract. Said composition being terbutaline, diphenhydramine and ranitidine.

6 Claims, No Drawings

EFFECT OF A COMBINATION OF A TERBUTALINE, DIPHENHYDRAMINE AND RANITIDINE COMPOSITION ON GASTROINTESTINAL INJURY PRODUCED BY NONSTEROIDAL ANTI-INFLAMMATORY COMPOSITIONS

This application is a continuation of Application Ser. No. 598,580, filed Oct. 15, 1990, now abandoned which is a continuation of U.S. Ser. No. 07/243,225, filed Sep. 2, 1988, now abandoned, which is a continuation of U.S. Ser. No. 06/894,982, filed Aug. 8, 1986, now abandoned.

This invention relates to nonsteroidal anti-inflammatory compositions containing, as protectants against gastrointestinal injury caused by said nonsteroidal anti-inflammatory drugs (hereinafter referred to as NSAID), combinations of a beta-adrenergic agonist and histamine-receptor blockers selected from the group consisting of $H_1$-and $H_2$-blockers and mixtures thereof. The compositions of this invention are useful in treating conditions and symptoms that are classically treated by the administration of NSAIDS, e.g., headache pain, pain and inflammation associated with arthritis and other systemic diseases, elevated body temperatures.

Aspirin and other NSAIDs have long been the most popular drugs for the management of pain, inflammation and fever in individuals. However, one of the drawbacks is the gastrointestinal injury and/or bleeding that sometimes accompanies their administration. This becomes a particular problem where large and sustained doses of NSAIDs must be given to control the symptoms, as for example, in the case of the management of arthritis.

It has now been found that NSAID-induced gastrointestinal injury can be significantly reduced when a combination of a betaadrenergic agonist and a histamine-receptor blocker selected from the group consisting of histamine $H_1$-, $H_2$-receptor blockers and mixtures thereof is administered concurrently with said NSAID.

As pointed out in U.S. Pat. No. 4,496,511, $H_1$- and $H_2$-receptor blockers form two well-known and distinct classes of pharmacologically active drugs that serve as blocking agents for histamine at $H_1$- and $H_2$- receptor sites, respectively. Histamine-receptor sites have been differentiated on the basis of the classes of antihistamines that can serve to block these sites. The fact that a drug is identified as an antihistamine does not necessarily mean that it will be effective in blocking all the known histamine-receptor sites but may, in fact, be selective so that it will act at one site e.g. $H_1$ site but not at another, e.g., $H_2$ site.

It has been reported in prior art that $H_2$-receptor blocking agents protect against aspirin-induced lesions in certain laboratory animals. One such study is reported in Gastroenterology Vol. 88, No. 5 part 2. p. 1344. It has also been reported that cyproheptadine has been evaluated as a protectant against aspirin-induced gastrointestinal injury (Indian J. Med. Res. 1980, 71, p. 926-32). Although cyproheptadine may have some $H_1$-receptor antagonist properties, it does not act exclusively at the $H_1$-receptor sites but rather acts predominantly to block the serotonin receptor sites. (Goodman and Gilman, "The Phamacological Basis of Therapeutics," Seventh Edition, p. 634).

Aside from the above, the present invention has further significant distinctions from the teachings in the Indian Journal. For one thing in this reference the aspirin and the cyproheptadine are not coadministered, as would be the case in the present invention. Furthermore, the treatment in this reference with cyproheptadine is reported as not modifying the gastric acidity and is contrary to the observations made in connection with the present invention. Moreover, in the Indian, reference the cyproheptadine was administered by intraperitoneal injection prior to the intragastric administration of the aspirin. In contrast, the compositions of the present invention lend themselves to oral administration, at which time the NSAID and the combination $H_1$- and $H_2$-receptor blockers are coadministered.

Moreover, there is nothing in the prior art cited above to suggest the essential feature of the present invention, namely the use of the combination of a beta-adrenergic agonist along with the histamine $H_1$-and/or $H_2$-receptor blockers.

Numbers of $H_1$-and $H_2$-receptor blockers are known in the prior art which are useful for the purposes of the present invention. By way of illustrating the $H_1$-receptor blockers that may be employed herein, mention may be made of the following: ethanolamines (e.g. diphenhydramine or its hydrochloride salt; carbinoxamine or its maleate salt); ethylenediamines (e.g. tripelennamine or its hydrochloride or citrate salts); alkylamines (e.g. chlorpheniramine or its maleate salt, brompheniramine or its maleate salt); and piperazines (e.g. hydroxyzine or its hydrochloride or pamoate salts, cyclizine or its hydrochloride or lactate salts, etc.). To exemplify the $H_2$-receptor blockers that may be advantageously used in the practice of this invention, the following are given: cimetidine, ranitidine, famotidine.

The $H_1$-and $H_2$-receptor blockers may be used in the form of their bases or in the form of their pharmaceutically acceptable salts. When employed as salts, these will usually be acid-addition salts wherein the acid portion may be hydrochloric, maleic, ascorbic, citric, pamoic, lactic, tartaric, etc.

The beta-adrenergic agonists also form a fairly well-defined class of pharmaceutically effective compounds that are characterized by the fact that they act by stimulating betaadrenergic receptor sites. These receptor sites are of two types, referred to as the $\beta_1$, and $\beta_2$ sites. Beta-adrenergic agonists may act on one or the other or on both types of sites.

Numerous beta-adrenergic agonists are know in the prior art which are useful for the purposes of this invention. Of special interest is terbutaline which is a $\beta_2$ agonist. By way of illustrating other beta-adrenergic agonists that may be employed herein, the following are given: isoproterenol metaproterenol, and albuterol. All of these may be employed as such or as pharmaceutically acceptable salts.

The NSAIDs also form a well-known class of drugs that are anti-inflammatory analgesics. These have the common property of inhibiting the formation of prostaglandins which have a protective affect on the gastrointestinal mucosa. See Goodman and Gilman "The Pharmacological Basis for Therapeutics" 7th Edition, p. 678. It is because of this inhibiting effect that the oral administration of drugs of this class tends to result in gastrointestinal injury and/or bleeding and is at least part of the problem that the present invention seeks to reduce or eliminate.

Numbers of NSAIDs are known in the prior art to which the present invention has application. The most commonly known group is the salicylates of which aspirin is the prime example. A further group of NSAIDs that has utility in connection with the instant invention is the proprionic acid derivatives. Included in this group are, for example, ibuprofen and naproxen.

Still a further group of NSAIDS, employable herein, is the fenamates and compounds closely related to them structurally. These may be illustrated by such compounds as mefenamic acid, meclofenamate sodium, and diclofenac and its sodium salt. Also belonging to the class NSAIDs with which the present invention is concerned are the indole derivatives (e.g. indomethacin); pyrrole alkanoic acid derivatives (e.g. tolmetin); pyrazalone derivatives (e.g. phenylbutazone); oxicams (e.g. piroxicam).

It is contemplated that in the practice of the present invention the NSAID, the beta-adrenergic agonist, and the histamine-receptor blocker or blockers will be administered concurrently in a convenient product form. The essential ingredients of such products will be the histamine $H_1$-and/or $H_2$-receptor blocker, the beta-adrenergic agonist, and the NSAID. Over and above this, these products may also contain other ingredients which will, to a large extent, depend upon the particular dosage form of the product, e.g., tablets, capsules, powders, suspensions.

The quantity of $H_1$-receptor blocker that will be contained in the composition of this invention may vary somewhat. All that is required is that an effective amount be present so that the $H_1$-receptor blocker can make its contribution as a protectant against NSAID-induced gastrointestinal injury.

Similarly the quantity of $H_2$-receptor blocker in the present composition may also vary. Again, all that is required is that the amount employed be an effective quantity that will enable the $H_2$-receptor blocker to play its part as protectant.

The quantity of beta-adrenergic agonist that will be contained in the present composition may vary somewhat. Again, all that is required is that it be present in sufficient amount to function as a protectant for NSAID-induced gastrointestinal injury when employed with the other active ingredients that form part of the composition of this invention.

The NSAID will be contained in the composition of this invention at concentrations at which it is generally found in therapeutic NSAID compositions intended for oral administration. This will usually be a pharmaceutically acceptable analgesic/ anti-inflammatory dose.

The quantitative relationship of the NSAID, the beta-adrenergic agonist, and the histamine $H_1$-and/or $H_2$-receptor blockers contained in the products of the present invention may be expressed in terms of the average daily dose of these ingredients, e.g., mg/kg of body weight/day. These relationships are set forth in Table I below, the general and preferred ranges being specified therein. The ranges specified for the histamine $H_1$-and $H_2$-receptor blockers are those that apply when the $H_1$ or $H_2$ blocker is employed. When a combination of the $H_1$ and $H_2$ blocker is utilized the amount of each contained in the product will be adjusted.

TABLE I

| Ingredient | General Range low | General Range high | Preferred Range low | Preferred Range high |
|---|---|---|---|---|
| NSAID | 10 mg/kg/day–100 mg/kg/day | | 15 mg/kg/day–75 mg/kg/day | |
| Beta-Adrenergic Agonist | 0.3 µg/kg/day–500 mg/kg/day | | 0.01 mg/kg/day–10 mg/kg/day | |
| Histamine $H_1$-Receptor Blocker (when employed) | 2.5 µg/kg/day–500 mg/kg/day | | 100 ug/kg/day–500 mg/kg/day | |
| Histamine $H_2$-Receptor Blocker (when employed) | 10 µg/kg/day–1 g/kg/day | | 0.01 mg/kg/day–10 mg/kg/day | |

The unit dosage forms for the present invention will be formulated for convenient oral administration. The range of the quantities of each ingredient is set forth in Table II below. The ranges specified for the histamine $H_1$-and $H_2$-receptor blockers are those that apply when the $H_1$ blocker or the $H_2$ blocker is employed. When a combination of the $H_1$ and $H_2$ blockers is utilized the amount of each in the product will be adjusted.

TABLE II

| INGREDIENT | UNIT DOSAGE mg/dose |
|---|---|
| NSAID | 200 mg–600 mg |
| Beta-Adrenergic Agonist | 0.7 mg–70 mg |
| Histamine $H_1$-Receptor Blocker (when used) | 0.01 mg–70 mg |
| Histamine $H_2$-Receptor Blocker (when used) | 0.5 mg–350 mg |

Depending upon the dosage form employed, the products of this invention may also contain other adjuvants that may be useful in formulating or administering the particular dosage form. Thus for example, when administered as a tablet, the products of this invention may also contain lubricants, excipients, binding agents, disintegrating agents, flavoring agents. In addition, these products may also contain other pharmaceutically active ingredients such as: decongestants, analgesic adjuvants, expectorants, antitussives, diuretics, other analgesics, other anti-inflammatory agents, antipyretics, anti-rheumatics, anti-oxidants, vasodilators, smooth musclerelaxants, skeletal muscle relaxants, bronchodilators, vitamins, trace minerals, amino acids, and biological peptides.

As indicated above, the products of the present invention may assume the form of tablets. However, they may also be formulated as caplets or be in powdered or granular form contained in edible capsules such as gelatin capsules. The present products may also be made up as suspensions or solutions of the above ingredients in a suitable liquid medium or as powders packaged in suitable paper envelopes.

The following examples are given to further illustrate the present invention. It is to be understood, however, that this invention is not limited thereto.

EXAMPLE 1

| Aspirin | 325 mg |

-continued

| | |
|---|---|
| Diphenhydramine hydrochloride | 16.67 mg |

The above ingredients are mixed in powdered or granular form and loaded into gelatin capsules.

EXAMPLE 2

| | |
|---|---|
| Aspirin | 325 mg |
| Ranitidine hydrochloride | 3.33 mg |

Prepared as described in Example 1.

EXAMPLE 3

| | |
|---|---|
| Aspirin | 325 mg |
| Metaproterenol sulfate | 0.83 mg |

Prepared as described in Example 1.

Dosage

Two capsules every 4 hours as needed. Do not exceed 8 capsules in 24 hours or give to children 12 or under, unless directed by a physician.

The following experiments were carried out to test the effectiveness of the combination of beta-adrenergic agonists with histamine $H_1$- or $H_2$-receptor blockers in protecting the stomach against NSAID-induced gastrointestinal injury. In these studies the histamine $H_1$-receptor blocker employed was diphenhydramine and it was used in the form of its HCl salt. The histamine $H_2$-receptor blocker utilized was ranitidine also employed in the form of its HCl salt. The beta-adrenergic agonist, exemplary of the present invention that was used in this test, was terbutaline. This was employed as the base.

A standard dose of 975 mg of aspirin is administered orally to obtain a benchmark for gastrointestinal injury. The histamine $H_1$- and $H_2$-receptor blockers and the beta-adrenergic agonists were tested separately along with the standard dose of 975 mg of aspirin for purposes of comparison with the irritation results obtained from the combination of the beta-adrenergic agonist with the histamine $H_1$- or $H_2$-receptor blocker when the administered with the standard test dose of 975 mg of aspirin.

The stomach lining of dogs is examined endoscopically and rated as to the degree of injury. The results are summarized in the tables following the description of the methodology which is given immediately below.

All test formulations are prepared on the day of the tests. The capsules are placed in the back of the dog's throat. A stomach catheter, with funnel attached, is positioned in the dog's stomach and 50 ml of deionized water is administered.

Healthy adult beagle dogs of either sex are selected for testing. Dogs are housed individually in stainless steel cages with grid floors to allow excreta to pass through. Room temperature in the holding rooms and test laboratories is maintained between 65° F. and 85° F. and relative humidity between 30% and 80%. Room lights remain on from 6:00 AM to 4:00 PM.

Each dog is trained to stand in a stanchion with sling support and to accept a bit tied in its mouth. A gastroscope is then passed through the bit into the dog's stomach. This training requires ten days to two weeks in most dogs.

To determine whether a dog is suitable for test purposes, its stomach is examined for a normal mucosa, and its gastric responsiveness to NSAID is evaluated (as under Test Procedure). An acceptable dog must have a gastric irritation score of 5 or greater, in the antrum 2 hours after dosage.

Food is withheld from test dogs for 24 hours before the test and during the test and water is allowed ad lib. The dogs are moved into a holding area away from the kennel. Fasted dogs of either sex are examined gastroscopically to ensure that their stomachs have normal healthy mucosal linings. The dogs are dosed orally with test formulations, which are flushed into their stomachs with 50 ml of deionized water. They are then re-examined two and four hours later for gastric petechiae and other signs of bleeding according to the following scale:

0 = uniform, pale to dark pink mucosa
1 = darker pink or blotchy mucosa
2 = petechiae and/or light red streaks
3 = few small lesions
4 = many or connected small lesions (striations)
5 = few large lesions
6 = many large lesions
7 = massive hemorrhagic damage Severity of injury for each treatment and at each time is calculated as the mean gastric irritation score.

In addition to the endoscopic observation of the gastric mucosa of each dog, a qualitative description of gastric fluid is recorded and a pH measurement is made of the gastric fluid. All of these are done 2 hours after administration of the test product.

A base line is established by measuring the various parameters after the administration of 975 mg of aspirin by itself. The resting normal stomach has an irritation score of 0 and a pH of 5 to 5.5. Aspirin produces injury which scores at approximately 5.6 after 2 hours and the gastric pH at this time is about 3.1.

TABLE III

Nonsteroidal Anti-inflammatory Compositions Protected Against Gastrointestinal Injury with a Combination of Certain Beta - Adrenergic Receptor Agonists and Histamine $H_1$-Receptor Blocker:
Data Summary

| | | 2-Hour Data | |
|---|---|---|---|
| | (N) | Irritation Score | pH |
| Aspirin 975 mg | 8 | 5.5 | 3.3 |
| Terbutaline 1.25 mg + Aspirin 975 mg | 4 | 4.0 | 2.9 |
| Terbutaline 2.50 mg + Aspirin 975 mg | 4 | 2.0 | 3.8 |
| Terbutaline 5.00 mg + Aspirin 975 mg | 8 | 1.4 | 4.0 |
| Terbutaline 10.0 mg + Aspirin 975 mg | 5 | 1.2 | 4.6 |
| Diphenhydramine 12.5 mg + Aspirin 975 mg | 4 | 5.5 | 1.4 |
| Diphenhydramine 25.0 mg + Aspirin 975 mg | 4 | 5.75 | 2.1 |
| Diphenhydramine 50.0 mg + Aspirin 975 mg | 4 | 4.0 | 3.6 |
| Terbutaline 2.5 mg + Diphenhydramine 50 mg + Aspirin 975 mg | 4 | 4.50 | 2.8 |
| Terbutaline 5.0 mg + Diphenhydramine 25 mg + Aspirin 975 mg | 4 | 1.75 | 4.4 |
| Terbutaline 5.0 mg + Diphenhydramine 50 mg + Aspirin 975 mg | 4 | 0.0 | 5.4 |

TABLE IV

Nonsteroidal Anti-inflammatory Composition Protected Against Gastrointestinal Injury with a Combination of Certain Beta-Adrenergic Agonists and Histamine $H_2$-Receptor Blockers. Data Summary

| | 2-Hour Data | | |
|---|---|---|---|
| | (N) | Irritation Score | pH |
| Aspirin 975 mg | 8 | 5.5 | 3.3 |
| Terbutaline 1.25 mg + Aspirin 975 mg | 4 | 4.0 | 2.9 |
| Terbutaline 2.5 mg + Aspirin 975 mg | 4 | 2.0 | 3.8 |
| Terbutaline 5.0 mg + Aspirin 975 mg | 8 | 1.43 | 4.0 |
| Terbutaline 10.0 mg + Aspirin 975 mg | 5 | 1.2 | 4.6 |
| Ranitidine 10 mg + Aspirin 975 mg | 6 | 3.50 | 5.3 |
| Ranitidine 20 mg + Aspirin 975 mg | 8 | 1.88 | 5.9 |
| Ranitidine 50 mg + Aspirin 975 mg | 6 | 0.67 | 6.1 |
| Terbutaline 5 mg + Ranitidine 10 mg + Aspirin 975 mg | 4 | 0.0 | 4.8 |
| Terbutaline 5 mg + Ranitidine 5 mg + Aspirin 975 mg | 4 | 1.75 | 4.1 |
| Terbutaline 2 mg + Ranitidine 5 mg + Aspirin 975 mg | 4 | 1.75 | 4.3 |

What is claimed is:

1. A composition for effectively reducing non-steroidal, anti-inflammatory, drug-induced, gastrointestinal irritation comprising:
   (a) a selective beta-adrenergic agonist selected from the group consisting of terbutaline and its pharmaceutical salts; and
   (b) a receptor blocking component agonist selected from the group consisting of histamine-$H_1$-receptor blockers, histamine $H_2$-receptor blockers, and combinations thereof, wherein the histamine-$H_1$-receptor blocker is selected from the group consisting of diphenhydramine and its pharmaceutical salts, and the histamine-$H_2$-receptor blocker is selected from the group consisting of ranitidine and its pharmaceutical salts; and
   wherein the concentration ratio of said agonist to said histamine-$H_1$-receptor blocker is from 1:5 to 1:10, and the concentration ratio of said agonist to said histamine-$H_2$-receptor blocker is from 1:1 to 1:2.5.

2. A method of effectively reducing the gastrointestinal irritation which results from the administration of non-steroidal anti-inflammatory agents which comprises the step of concurrently administering to a patient in need thereof a composition comprising:
   (a) a selective beta-adrenergic agonist selected from the group consisting of terbutaline and its pharmaceutical salts; and
   (b) a receptor blocking component agonist selected from the group consisting of histamine-$H_1$-receptor blockers, histamine $H_2$-receptor blockers, and combinations thereof, wherein the histamine-$H_1$-receptor blocker is selected from the group consisting of diphenhydramine and its pharmaceutical salts, and the histamine-$H_2$-receptor blocker is selected from the group consisting of ranitidine and its pharmaceutical salts; and
   wherein the concentration ratio of said agonist to said histamine-$H_1$-receptor blocker is from 1:5 to 1:10, and the concentration ratio of said agonist to said histamine-$H_2$-receptor blocker is from 1:1 to 1:2.5.

3. The composition of claim 1 wherein said receptor blocking component is the histamine-$H_1$-receptor blocker diphenhydramine 4. The composition of claim 1 wherein said receptor blocking component is the histamine-$H_2$-receptor blocker ranitidine.

5. The method of claim 2 wherein said receptor blocking component is the histamine-$H_1$-receptor blocker diphenhydramine.

6. The method of claim 2 wherein said receptor blocking component is the histamine-$H_2$-receptor blocker ranitidine.

* * * * *